(12) United States Patent
Simpson (10) Patent No.: US 10,143,577 B2
(45) Date of Patent: *Dec. 4, 2018

(54) INFLATABLE STRUCTURE WITH BRAIDED LAYER

(71) Applicant: C.R. BARD, INC., Murray Hill, NJ (US)

(72) Inventor: Charles L. Simpson, Westlake Village, CA (US)

(73) Assignee: C.R. BARD, INC., Tempe, AZ (US)

( * ) Notice: Subject to any disclaimer, the term of this patent is extended or adjusted under 35 U.S.C. 154(b) by 6 days.

This patent is subject to a terminal disclaimer.

(21) Appl. No.: 15/262,767

(22) Filed: Sep. 12, 2016

(65) Prior Publication Data

US 2016/0374841 A1    Dec. 29, 2016

Related U.S. Application Data

(63) Continuation of application No. 12/444,796, filed as application No. PCT/US2007/081264 on Oct. 12, 2007, now Pat. No. 9,440,055.

(60) Provisional application No. 60/829,231, filed on Oct. 12, 2006.

(51) Int. Cl.
*A61M 25/10* (2013.01)
*A61F 2/958* (2013.01)
*A61M 29/02* (2006.01)
*D04C 1/02* (2006.01)

(52) U.S. Cl.
CPC ............ *A61F 2/958* (2013.01); *A61M 25/10* (2013.01); *A61M 25/1002* (2013.01); *A61M 25/104* (2013.01); *A61M 25/1029* (2013.01); *A61M 25/1038* (2013.01); *A61M 29/02* (2013.01); *D04C 1/02* (2013.01); *A61F 2250/0018* (2013.01); *A61F 2250/0039* (2013.01); *A61M 25/1011* (2013.01); *A61M 2025/1004* (2013.01); *A61M 2025/1031* (2013.01); *A61M 2025/1075* (2013.01); *A61M 2025/1079* (2013.01); *A61M 2025/1084* (2013.01); *D10B 2403/02411* (2013.01); *D10B 2509/06* (2013.01)

(58) Field of Classification Search
CPC .. A61M 2025/1084; A61M 2025/1059; A61M 25/1038; A61M 25/104
See application file for complete search history.

(56) References Cited

U.S. PATENT DOCUMENTS

| | | | | |
|---|---|---|---|---|
| 5,853,389 A | * | 12/1998 | Hijlkema | A61M 25/1002 604/103.07 |
| 6,221,006 B1 | * | 4/2001 | Dubrul | A61B 17/221 600/159 |
| 2002/0010489 A1 | * | 1/2002 | Grayzel | A61F 2/958 606/194 |
| 2006/0085022 A1 | * | 4/2006 | Hayes | A61M 25/104 606/192 |

* cited by examiner

*Primary Examiner* — Diane Yabut
(74) *Attorney, Agent, or Firm* — King & Schickli, PLLC (57) ABSTRACT

A balloon for medical treatments such as percutaneous transluminal coronary angioplasty (PTCA), delivery of a vascular stents or stent grafts, employs reinforcement materials that are patterned so as to promote consistent folding of the balloon. Methods and apparatus for biocidal treatment using such a balloon, including balloons with fiber fabric reinforcements.

9 Claims, 9 Drawing Sheets

0°-Yarn may be sandwiched between diagonals.

Fig. 4A

⤫ means ╱ yarn in front
⤬ means ╲ yarn in front

INFLATABLE STRUCTURE WITH BRAIDED LAYER

PRIORITY CLAIM AND INCORPORATION BY REFERENCE

The present application claims priority to U.S. Provisional Application Ser. No. 60/829,231, filed Oct. 12, 2006, hereby incorporated by reference in its entirety.

TECHNICAL FIELD

The invention relates to composite structures for medical balloons and in particular, such structures that promote predictable folding.

BACKGROUND ART

Woven and braided fabrics have been used to reinforce various devices. Compared to weaving, braiding may impart greater strength for a unit of weight. The strength of a braid comes from the fact that multiple yarns can be intertwined without any being twisted around another. Generally these are continuously braided at an angle and there is no need for any yarn to suffer a sharp bend. As a result, loads may be distributed evenly and efficiently throughout the braid.

Automated fabrication of braids generally results in tubular or flat configurations. Braids can also be formed without any underlying support (freestanding) or over a mandrel or a part to be reinforced, such as the mast of a sailboat. Braiding can also be done over a three-dimensional part, such as a tool.

A single braid can incorporate multiple yarn materials to form a hybrid weave. This is often done to make patterns in the resulting product. Yarns can be of metal, carbon fiber, glass fiber, mono or multifilament threads, etc. Braiding can be done with very delicate materials.

Braid has been used as a reinforcement for some surgical devices such as endoscopes and catheters and for implantable devices such as splints and stents.

Non-woven fiber reinforcements are also known, for example, randomly arrayed fibers such as in fiberglass and hand-laid fibers arrayed over and within a matrix are known strategies. Both have been described in connection with the reinforcement of medical balloons.

Many composite balloon structures are reinforced by inelastic filaments, which is a good match for folding to minimize the collapsed balloon's volume. However, the fiber can be an impediment to folding, an issue that is addressed by at least some of the inventive embodiments disclosed below.

The following are some references to background in the field of braiding technology. A brief overview and comparison of 2D and 3D braiding machines and the kinds of structures they can create is provided by an article, "Braiding," 2005 Advanced Composite Materials & Textile Research Laboratory, University of Massachusetts-Lowell. [online] August 2007 [Retrieved on 2006 Jun. 21]. Retrieved from the Internet. <http://mechanical.uml.edu/acmtrl/research-Braiding.htm>.

The company, 3TEX, provides information about state of the art three-dimensional automated braiding at [online]] Retrieved on 2005 Jun. 21] Retrieved from the Internet <http://www.3tex.com/3braid.cfm>. The page shows photographs and an animation of a large Cartesian braiding machine. One of the points made is that with computer control, it is possible to shift the braiding pattern at any time without changing the number or continuity of the yarns.

A report by the National Textile Center (NTC) in Springhouse, Pa. discusses different kinds of braiding patterns such as diamond, regular, and Hercules braids and discusses behavior of braids under tensile load, the effect of yarn angle with respect to load and jamming condition, and other issues. "Engineered Non-Linear Elastic Blended Fabrics," NTC Project F00-PH05 2005 [Retrieved on 2006 Jun. 21]. Retrieved from the Internet. <http://www.ntcresearch.org/pdf-rpts/AnRp02/F00-PH05-A2.pdf>

The following articles discuss braids with different mechanical properties, including mixing materials. "Analysis of three-dimensional textile preforms for multidirectional reinforcement of composites;" Guang-Wu Du, Tsu-Wei Chou and P. Popper; J. Mater. Sci. 26 (1991) 3438-3448. Dunn, Matthew; Armstrong-Carroll, Eileen; Gowayed, Yasser; "Engineered Non-linear Elastic Bland Fabrics" [Retrieved on 2006 Jun. 21]. Retrieved from the Internet. <http://wwvv.ntcresearch.org/pdf-rpts/Bref0601/F00-P05.pdf>.

The following article discusses the effect of braids on the mechanical properties of braided fabrics. There is considerable background on hybrid braids and their performance. Seneviratne, Waruna P. and Tomblin, John S.; "Design Of A Braided Composite Structure With A Tapered Cross-Section;" National Institute for Aviation Research Wichita State University Wichita, Kans. 67260-0093 The Department Of Defense Handbook Composite Materials Handbook Volume 2, "Polymer Matrix Composites Materials Properties," discusses braids in the context of composite materials. [Retrieved on 2006 Jun. 21]. Retrieved from the Internet. <http://www.lib.ucdavis.edu/dept/pse/resources/fulltext/HDBK17-2F.pdf>

DISCLOSURE OF INVENTION

A balloon for medical treatments such as percutaneous transluminal coronary angioplasty (PTCA), delivery of a vascular stents or stent grafts, employs reinforcement materials that are patterned so as to promote consistent, predictable, or tighter, folding of the balloon.

The invention provides a medical balloon whose walls have relatively stiff and relatively flexible regions to promote folding along the flexible regions. The variation in stiffness is achieved, according to the different embodiments, by variably arranging composite elements on, or within, the wall of the balloon; by adding stiffening members to the wall at selected portions; by varying the properties of a fabric or braid or other filamentous structure to define variable stiffness, and by other means.

According to an embodiment, the invention is a foldable composite balloon with a wall. The wall has first and second filaments and first and second wall portions. The wall has compression elements separating the first and second filaments in the first wall portions so that they define opposing tension elements running in a wind direction. The opposing tension elements have a component in a specified direction and are separated by the at least one compression element resulting in the first portion being stiffer than the second portion, at least in the specified direction, the first and second portions being arranged such that when the balloon is folded, the first portions resist bending more than the second portions. This may be so the folds are generally aligned with the second portions and it may help to ensure a neat and predictable folding behavior when the balloon is collapsed. This in turn can help to ensure a compact configuration in tight areas.

Variations of this embodiment and others are possible. For example, the first and second filaments may be portions of elongate members that run continuously through the first portions and the second portions. The first and second filaments may be braided to define at least a portion of a braid. The braid may include a triaxial portion having third filaments running as a 0° braid yarn in the first and second portions, the third filaments in the first portions being thicker than the third filaments in the second portion and the third filaments forming at least part of the at compression element. Note, the 0° yarn refers to yarns running in a longitudinal direction, which is the direction along which the braid extends (or gets longer) as the braid is woven.

The first and second filaments may define at least a portion of a braid having, within the second portions, a greater number of crossings between layer alternations than within the first portions. The first and second filaments may define at least a portion of a biaxial braid having, within the second portions, a greater number of crossings between layer alternations than within the first portions.

The wall may be elongated such as to have a longitudinal axis and the second portion may be aligned with the axis or follow a helical path around the longitudinal axis. The wall may include a matrix, such as a polymer matrix, and members embedded therein with the first and second filaments being embedded in the matrix and the members forming at least portions of the compression elements.

The wall may include a matrix and flat members embedded therein, the first and second filaments being embedded in the matrix and the members forming at least portions of the compression element.

According to an embodiment, the invention may also provide a foldable composite balloon with a wall of polymer matrix with first and second filaments attached to it. The wall may have first and second portions, the first and second filaments spaced apart by a portion of the polymer matrix in the first wall portions, such that they define opposing tension elements running in a wind direction having a component in a specified direction and separated by the matrix portion. The spacing of the tension elements on opposite sides of the matrix portion is such that the matrix portion acts as a compression element and the result is that the first portion is stiffer than the second portion, at least in the specified direction. The first and second portions may be arranged such that when the balloon is folded, the first portions resist bending more than the second portions. Or the second portions may be aligned with folding lines of the balloon so the structure helps to promote folding or creates a natural folding behavior.

This embodiment has variations as well, such as may include the first and second filaments being portions of elongate members running continuously through the first portions and the second portions. The first and second filaments may be braided to form a braid. The first and second filaments may define a braid having, within the second portions, a greater number of crossings between layer alternations than within the first portions. The second portions may define folding contours and the alternations are staggered in the first region such that no consecutive trains of side alternations occur that are parallel to the folding contours.

According to yet another embodiment, the invention is a foldable composite balloon with a body that has a polymer matrix and a filamentous structure attached thereto. The body may have first and second portions and folding lines with the filamentous structure defining first and second portions, the folding lines lying within the second portions and the first portions lying between the second portions. In one embodiment, the filamentous structure may be configured to promote folding along the folding lines either by being configured to cause the body to be stiffer in the first regions, at least in a direction perpendicular to the folding line, than the second portions. In another embodiment, the filamentous structure may be configured to generate a mechanical bias that favors folding along the folding lines as a result of being formed over a form with edges on it.

The filamentous structure may be configured to cause the body to be stiffer in the first regions, at least in a direction perpendicular to the folding lines, than the second portions. The filamentous structure may include a braid. The filamentous structure may have first and second filaments and a compression element, the first portions being stiffer, at least in a direction perpendicular to the folding lines, at least in part as a result of the first and second filaments of the first portions being arranged with the compression element between then, thereby defining opposing tension elements separated by the compression element. The braid may have layers with more layers in the first portions than in the second portions such that the first portions are stiffer than the second portions.

The body may have a longitudinal axis and the folding lines are parallel to the longitudinal axis. The body may have a longitudinal axis and the folding lines may wind helically around a longitudinal axis. The braid may be triaxial or biaxial.

According to yet another embodiment, a foldable composite balloon is provided which has a wall with a polymer matrix included elements attached to, or within, the polymer matrix. The included elements are arranged to define first portions, and second portions of the wall such that the wall folds more readily in the first portions than the second portions.

According to yet another embodiment, a foldable composite balloon is provided with a wall having elongate reinforcement members, first portions, and second portions, the stiffness of the first portions being lower than the stiffness of the second portions. An arrangement of the elongate reinforcement members causes the wall to be stiffer in the second portions than in the first portions, whereby the balloon tends to fold along contours coinciding with the low stiffness portions.

According to an embodiment, the invention is a method for the treatment of an infected area within a body. The method includes applying an electrically conductive biocide composition to an infected area within the body that has been exposed during surgery, and applying an electric field to the biocide composition by contacting a surface with the biocide composition with an inflatable member having conductive surface of alternate polarity to generate an electric field. The electric field strength and duration of application are sufficient to produce killing of microorganisms in the infected area. Preferably, the infected area is composed of a biofilm that is composed predominately of bacteria, yeast or fungus. Preferably, the biocide is an antibiotic selected from the family of antibiotics consisting of penicillins, cephalosporins, aminoglycosides, tetracyclines, sulfonamides, macrolide antibiotics and quinolones. Preferably, the electrically conductive biocide composition is a buffered saline composition. Preferably, the biocide composition includes a thickener. Preferably, the electric field is substantially constant. Preferably, the electrical field is a pulsed or alternating electric field. Preferably, the electric field strength is generated by currents having a value in the range from about 1 to about 200 milliamps. Preferably, said electric field is applied to the electrically conductive biocide composition for a period of time of between about 1 minute to about 48 hours. Preferably, the biocide is present in the composition, in an amount which would be ineffective to completely kill the infected area if used in the absence of the electric field.

In a particular variation of the above method embodiments, the method is performed during the course of heart valve replacement surgery. Preferably, the biocide is an antibiotic, an anti-fungal agent, a disinfectant, a sterilant, other antiseptic agents, hexachlorophene, cationic bisiguanides, iodine, iodophores, para-chloro-meta-xylenol, triclosan, furan preparations, methenamine, aldehydes, or alcohols. Preferably, the cationic bisiguanides include chlorhexidene or cyclohexidene. Preferably, iodine include povidone-iodine. Preferably, iodophores include povidone-iodine. Preferably, furan preparations include nitrofurantoin or nitrofurazone. Preferably, aldehydes is in glute form.

According to another embodiment, the invention is a medical balloon, comprising: a balloon body having an array of reinforcement fibers exposed on an external surface thereon; at least some of the reinforcement fibers being electrically conductive subsets of which are connectable to a source of voltage such that an electric field can be continuously generated on the surface of the body. Preferably, the fibers form a braided pattern. Preferably, the at least some of the reinforcement fibers are of metal. Preferably, the at least some of the reinforcement fibers are zero-angle fibers of a triaxial braid.

According to an embodiment, the invention may also provide a foldable composite balloon with a wall of polymer matrix with first and second filaments attached to it. The wall may have first and second portions, the first and second filaments spaced apart by one or more radio-opaque elements in the first wall portions, such that the yarns overlying them define opposing tension elements running in a wind direction having a component in a specified direction and separated by the radio-opaque portions. This allows the radio-opaqu included elements to be relatively stiff without impeding (in fact promoting) the folding of the balloon. The spacing of the tension elements on opposite sides of the matrix portion is such that the included radio-opaque elements act as compression elements and the result is that the first portion is stiffer than the second portion, at least in the specified direction. The first and second portions may be arranged such that when the balloon is folded, the first portions resist bending more than the second portions. Or the second portions may be aligned with folding lines of the balloon so the structure helps to promote folding or creates a natural folding behavior.

This embodiment has variations as well, such as may include the first and second filaments being portions of elongate members running continuously through the first portions and the second portions. The first and second filaments may be braided to form a braid. The first and second filaments may define a braid having, within the second portions, a greater number of crossings between layer alternations than within the first portions. The second portions may define folding contours and the alternations are staggered in the first region such that no consecutive trains of side alternations occur that are parallel to the folding contours.

In another embodiment, a foldable composite balloon has a braided reinforcement structure defining a wall. The braided reinforcement pattern is such that the wall is stiffer at the first wall portions than at the second wall portions. The first and second wall portions are arranged such that when the balloon is folded, the first portions resist bending more than the second portions. Preferably, at least the first wall portions have a radio-opaque coating thereon. Alternatively, only the first wall portions have a radio-opaque coating thereon. In another preferred embodiment, a radio-opaque material is integrated in the first portions only.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

MODE(S) FOR CARRYING OUT THE INVENTION

The various embodiments will be described in detail with reference to the accompanying drawings. Wherever possible, the same reference numbers will be used throughout the drawings to refer to the same or like parts.

Figure 1:
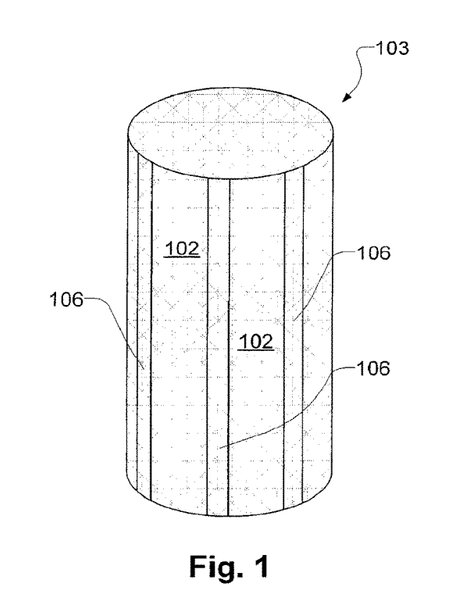
FIG. 1 shows a reinforcement structure, such as a tube braid, that may be used in a composite balloon, the reinforcement structure having relatively flexible portions or facets and relatively stiff portions or facets.

FIG. 1 shows a reinforcement structure, such as a tube braid, that may be used in a composite balloon, the reinforcement structure having relatively flexible portions 106 or facets and relatively stiff portions 102 or facets. A tubular braid 103 has stiff portions 102 that are relatively stiff, or at least relatively stiff in the circumferential direction (i.e., the direction about the balloon axis). The tubular braid 103 also has flexible portions 106 that are flexible relative to the stiff portions 102, also, at least in the circumferential direction.

Figure 2A:
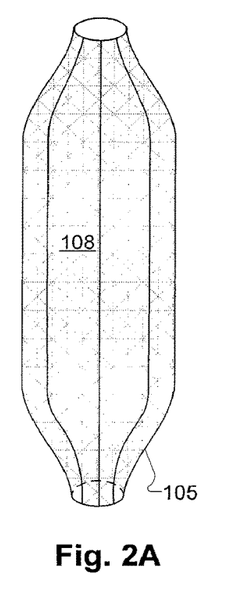
FIGS. 2A and 2B are figurative illustrations of medical balloon fiber preforms with longitudinal folding patterns, the first being straight and the second being helical.

The tube braid 103 may be of strong filaments (not shown separately) of any type, but in the present embodiments of folding medical balloons, they include relatively inelastic high strength synthetic fibers. The filaments may be a mix of different materials and cross-sectional shapes and different materials may be combined in various ways as discussed below. The braiding may be done using a variety of mechanisms which are known in the art employing braid patterns and other structures described herein. For example, the braiding of the tube braid 103 may be performed using a programmable tube braider (not shown). Alternatively, the tube braid 103 may be a portion of a non-cylindrical (three-dimensional) braid as illustrated in FIG. 2A with progressively tapering ends. In such a case, the filaments may be braided over a three-dimensional form (for example, as at 220 in FIG. 5B, described below) to create a desired balloon shape.

The tube braid 103 may be embedded in, impregnated with, or otherwise combined with a flexible material that can hold pressure and ensure against leakage to form a medical balloon. For example, the tube braid may be glued over a base liner that has the shape of the desired kind of balloon. A variety of known processes for forming composite structures are suitable so the subject will not be expansively discussed here.

Figure 2B:
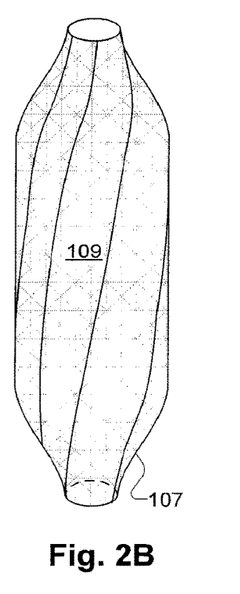

FIGS. 2A and 2B are figurative illustrations of medical balloon fiber preforms with longitudinal folding patterns. In FIG. 2A, balloon preform 105 has straight folding contours and in FIG. 2B, balloon preform 107 has helical folding contours. The preforms 105 and 107, as described below with reference to FIGS. 5A and 5B, may be braided over a three-dimensional form to achieve the illustrated shape. The different portions with variegated flexibility, as identified above, are indicated collectively at 108 and 109. Note that a variety of other shapes may be used with the present inventive features and the shapes shown are merely for purposes of describing various folding features and structures.

Figure 3:
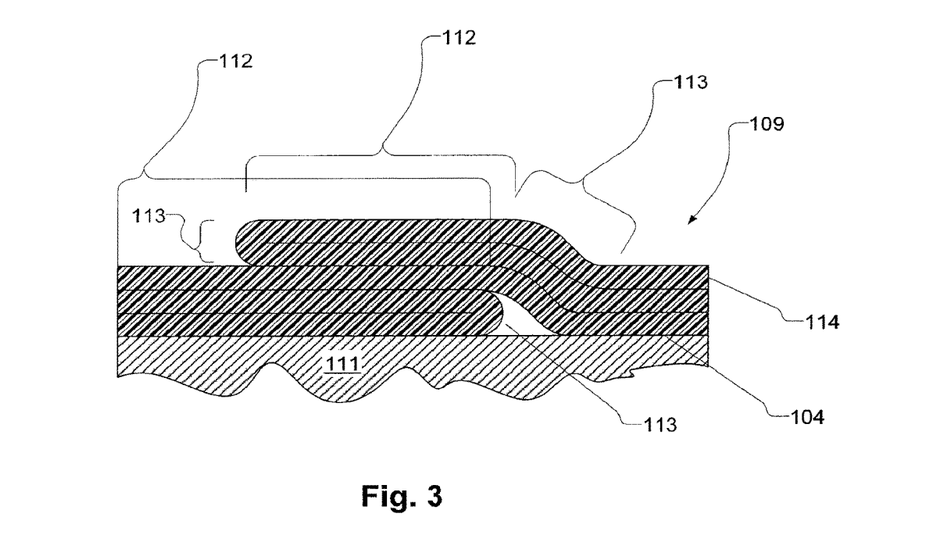
FIG. 3 is a planar development of a portion of folded balloon wall lying adjacent a catheter surface according to an embodiment of the invention.

FIG. 3 is a planar development of a portion of folded balloon wall lying adjacent a catheter surface according to an embodiment of the invention. As will be understood by those of skill in the art, a very low profile can be achieved in a medical balloon by configuring it to fold upon deflation. The folded shape shown in FIG. 3 shows a portion of the wall of a folded balloon 109. As indicated, the illustration is a planar development and it is to be understood that the surface indicated at 104 would wrap around the axis of the balloon which passes through the plane of the drawing, as would the overlying balloon wall 114 and folds. For example, the structure 111 may be a catheter with a circular cross-section. FIG. 3 shows how the relatively stiff portions 112 lie relatively flat while the folds coincide with the relatively flexible portions 113. As a result, when the balloon 109 is deflated, the fold pattern may be more readily assumed by the balloon 109. Though not illustrated, a composite fiber reinforcement, such as the braid discussed above, is preferably incorporated within the wall 114 of the balloon 109.

The embodiments described above and below may be modified in such a way that balloons may not be completely folded, in the sense that the wall is bent 180° and completely overlaps and contacts an adjacent portion, in order for the balloon to achieve a compact shape. That is, the wall may simply be wrap or bend without making a fully 180° turn and/or adjacent portions may not lap once in the folded configuration. In such embodiments, the portions of the wall that are stiffer will resist bending more than other portions. For example, in FIG. 3, portion 112 resists bending more than portion 113. Note that since FIG. 3 shows a planar development, portion 112 is generally wrapped around the axis of the balloon, even though it is represented as a flat portion. A balloon may have a relaxed condition in the folded state (in fact this may be preferred in some embodiments) in which case some parts of the balloon may actually provide a negative resistance to bending to form the folded configuration. So the term "resistance" here is used in a general sense that covers zero, negative, and positive resistance. In other words, it is understood that the portions of the balloon that are bent the most, such as in folding, may achieve their most relaxed state in, for example, a folded configuration, in which case, the balloon would not generate a positive resistance to folding because it tends to fold. So in that case, the resistance at certain portions, for example fold lines, would be negative.

Figure 4A:
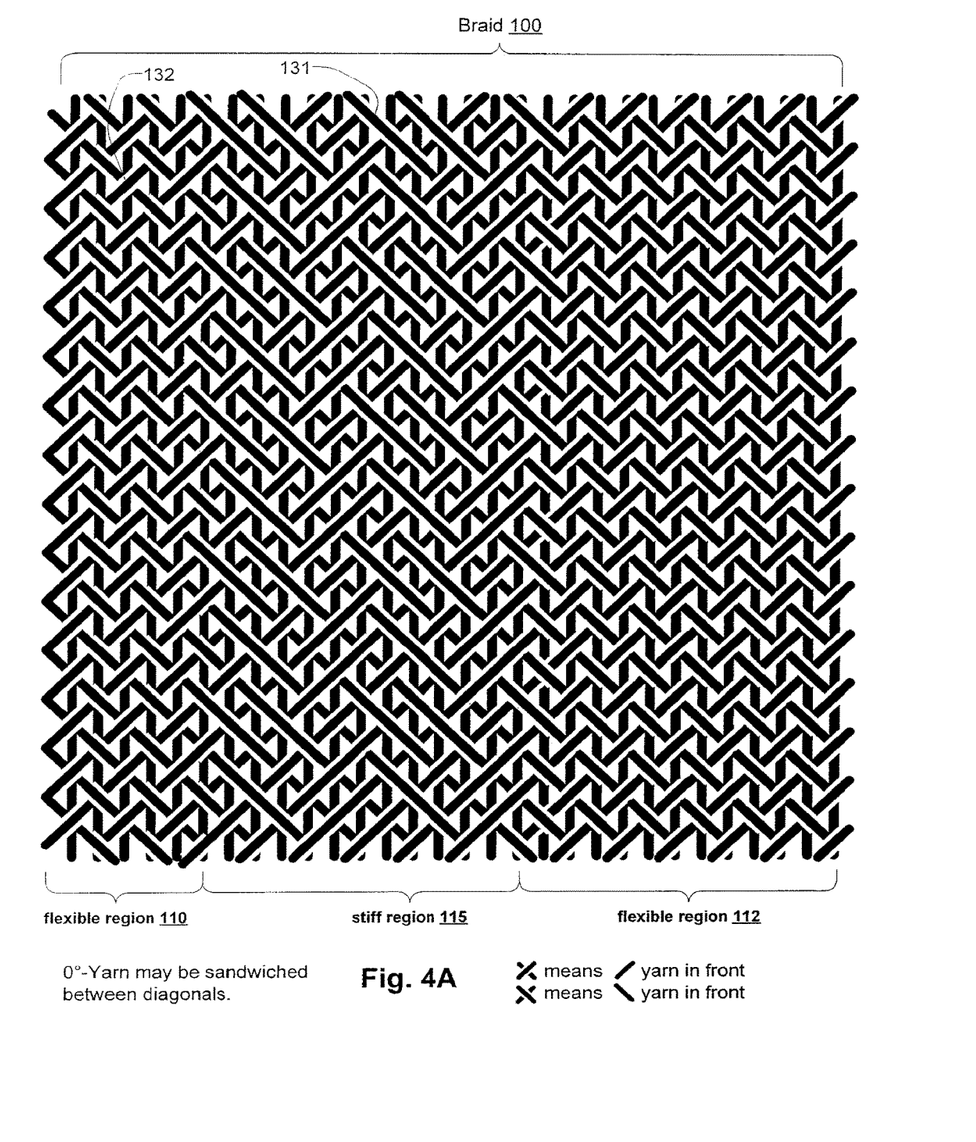
FIG. 4A illustrates a braiding pattern that provides relatively stiff and relatively pliable portions.

FIG. 4A illustrates a braiding pattern that provides relatively stiff and relatively flexible portions. FIG. 4A shows a triaxial braid fabric 100 that may form part of a reinforcement structure for the wall of a medical balloon (not shown in the present drawing). In a flexible region 110 and 112, which would coincide with regions 113 in FIG. 3, the braiding pattern is a so-called diamond braid pattern with the yarns alternating sides each time they cross a yarn. With the diamond braid pattern, longitudinal (longitudinal being defined as the direction of the long axis of the page which is also the long axis of the balloon) "seams" are formed where all the yarns cross sides along the same longitudinal line. This makes the diamond pattern easier to bend because the seams are thin offer less resistance. In the stiff regions 115 (only one shown, but there would ordinarily be more) yarns generally cross more than one 0° yarn before they cross sides. For example, in a Hercules braid, a yarn crosses three other 0° yarns before crossing sides. In the illustrated braiding pattern for the stiff region 115, the yarns cross three other 0° yarns before crossing. The pattern is preferably such that the crossing points lined up in the longitudinal direction lines.

Figures 4B, 4C, 5A:
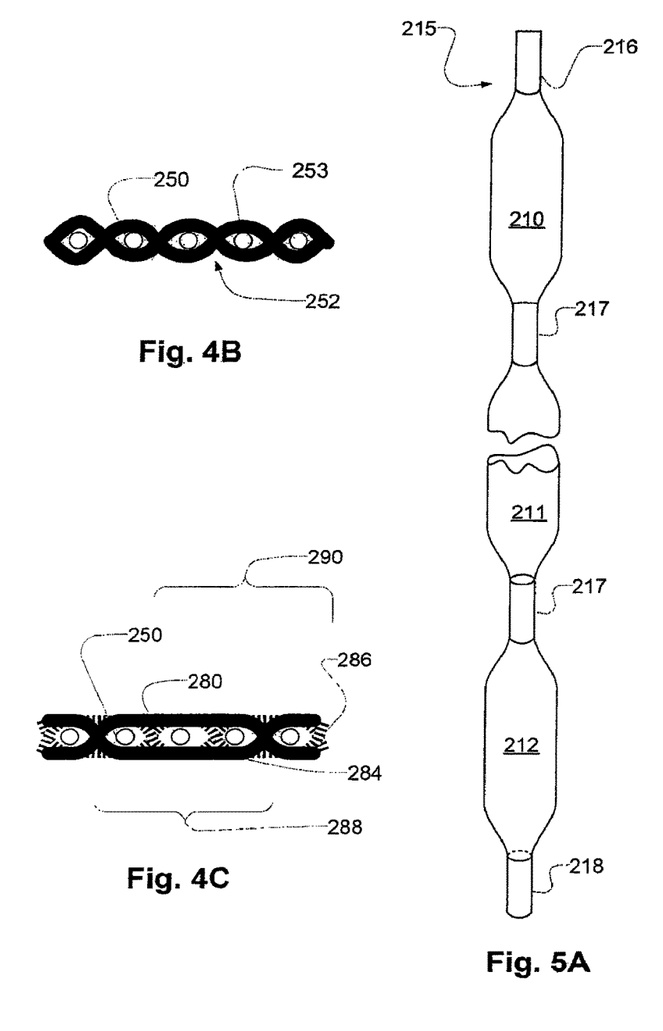
FIGS. 4B and 4C are illustrations for helping to explain a feature of the braid pattern of FIG. 4A.
FIG. 5A illustrates a multi-balloon mandrel that may be used for braiding or weaving multiple reinforcement structures for a balloon.

Refer now to FIGS. 4B and 4C, which illustrate how the braiding patterns of FIG. 4A of the flexible 110 and stiff 115 regions differ and how the differences contribute to relative stiffness. In FIG. 4B, the relatively flexible diamond pattern is shown in a figurative cross-section. The yarns 250, shown in section, represent longitudinal fibers of the axial braid. Note that the figure is a figurative cross-section because, although the yarns 253 cross at a diagonal and, at any straight cross-section, continuous runs of crossing yarns could not be seen in a real cross-section, the illustration is functionally similar, as may be confirmed by inspection. The seams, such as indicated at 252, where yarns 253 cross, are arranged in successive ranks along the longitudinal direction because yarns alternate at every crossing. In contrast, as shown in FIG. 4C, where yarns do not alternate at every crossing, a stiffer structure is formed with crossing yarns 280 and 284 form tension elements that, in combination with the embedded matrix (which resist compression) define a stiff segment 288. The positions of the crossing points of other crossing yarns such as those shown crossing at 286, do not coincide in the lateral direction (i.e., the crossing lines are not aligned along longitudinal lines) so there no seam arises where the braid would be easier to bend. Thus, for example, a stiff segment 290 (shown with broken lines) which is longitudinally adjacent the foreground stiff segment 288, is offset in the lateral direction. In this way, the stiffness is extended laterally beyond the range of the stiff segment 288. This kind of stiff arrangement is illustrated in FIG. 4A at 115.

FIG. 5A illustrates a multi-balloon form 215, or mandrel, that may be used for braiding (or weaving) multiple reinforcement structures for a balloon in a single braiding operation. A braid may begin at a top extension portion 216 and widen into a balloon portion 210 and then neck down to a connecting section 217A. The braiding operation may continue over balloon sections 211 and connecting section 217 (arbitrary number of them), and then over a final balloon section 212, and extension section 218, to form a structure (not shown) that may be cut into multiple balloon preforms.

Figure 5B:
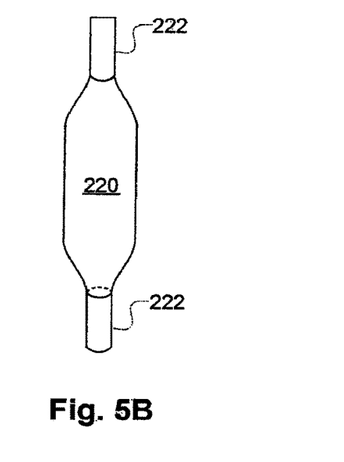
FIG. 5B illustrates a single-balloon mandrel that may be used for braiding or weaving a reinforcement structure for a balloon.
Figure 5C:
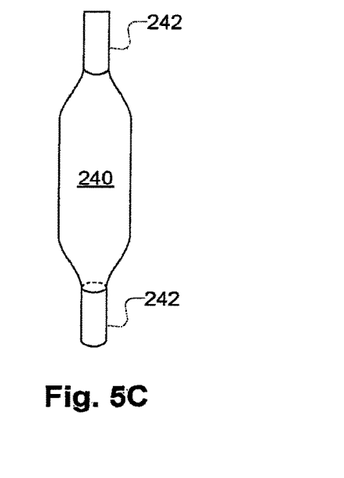
FIG. 5C illustrates a base balloon over which a reinforcement structure may be braided.

FIG. 5B illustrates a single-balloon form 220 with extension sections 222 that may be used for braiding (or weaving) a single reinforcement structure for a balloon. In both the 215 and 220 embodiments, the form may be made of a disintegrating, or otherwise collapsible structure to permit it to be removed from the finished form 215, 220 to leave one or more preforms. The cutting operation to divide the segments of embodiment 215 may be done before or after the collapsing of the form 215. FIG. 5C illustrates a base balloon over which a reinforcement structure may be braided. The base balloon 240 with extensions 242 may act as a liner portion of a finished balloon, functioning as a braiding form for fabrication of the braided structure and, optionally, then remaining as part of the finished balloon. Preferably, the base balloon 240 is fabricated of an inelastic material to facilitate its use as a form and base for braiding.

Figure 6A:
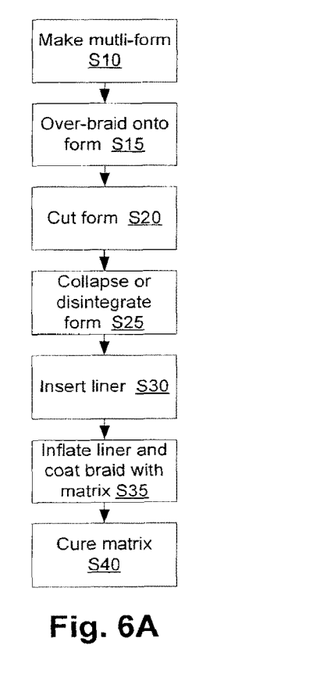
FIG. 6A is a flow diagram of a method for making a reinforced medical balloon using a multi-balloon form.

FIG. 6A is a flow diagram of an example of a method for making a reinforced medical balloon using a multi-balloon form. In step S10, the multiple part form 215 is fabricated and in step S15, a braiding device is used to braid over the form 215 (FIG. 5A). In step S20, the resulting form and braided preform are then cut into segments to define the individual preforms to be used in the separate balloons. In step S25, next, the underlying form is collapsed, for example by dissolving in acid or water, melting, reconfiguring, or performing some other step or steps depending on the structure of the form. In step S30, a liner is inserted in each balloon preform and inflated. The liner may be formed such that it assumes the desired shape and size when inflated. In step S35, in an embodiment, the liner is inflated with a pressurized fluid and the braided preform coated with a matrix which is cured in step S40 and which serves to adhere the preform, the liner balloon, and the matrix together, forming an integral structure.

Figure 6B:
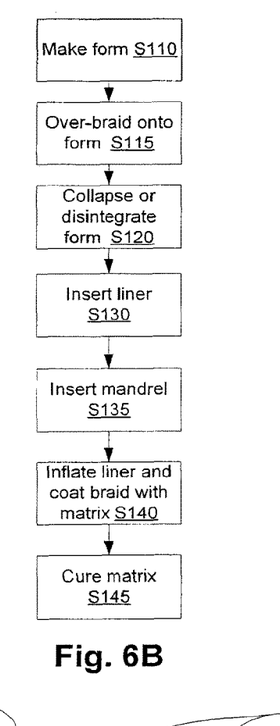
FIG. 6B is a flow diagram of a method for making a reinforced medical balloon using a single-balloon form.

FIG. 6B is a flow diagram of a method for making a reinforced medical balloon using a single-balloon form. In step S110, the form 215 is fabricated and in step S115, a braiding device is used to braid over the form 225 (FIG. 5B). In step S120, the underlying form is collapsed, for example by dissolving in acid or water, melting, reconfiguring, or performing some other step or steps depending on the structure of the form. In step S130, a liner is inserted in the balloon preform and inflated. The liner may be of a form and shape that requires molding before adopting its final shape. A cylindrical mandrel may be inserted in step S135 to help seal and fill the balloon. In step S140, in this embodiment, the liner is inflated with a pressurized fluid and then the braided preform coated with a matrix that is cured in step S145 and which serves to adhere the preform, the liner balloon, and the matrix together, forming an integral structure.

Figure 6C:
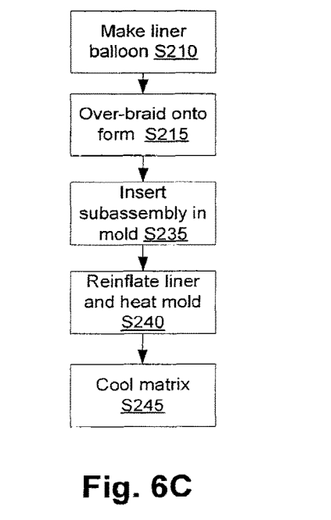
FIG. 6C is a flow diagram of a method for making a reinforced medical balloon using a liner balloon as a form.
Figure 7:
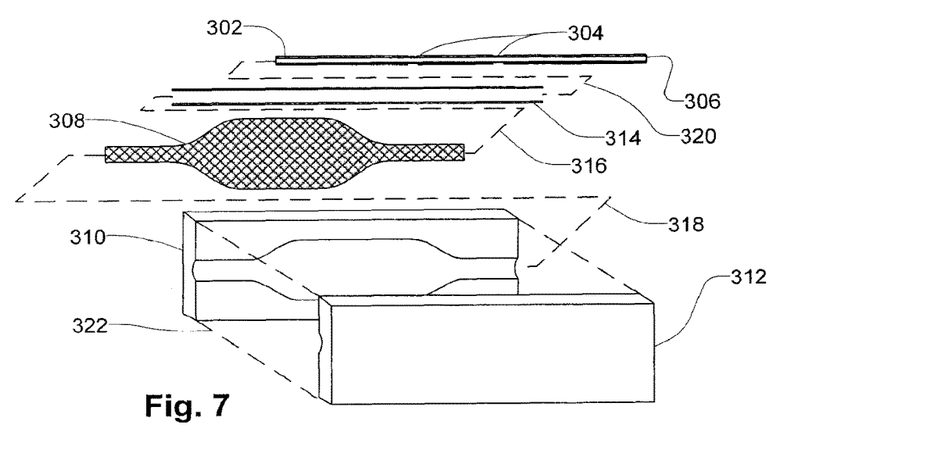
FIG. 7 illustrates elements used in manufacturing a composite balloon according to an embodiment.
Figure 8A:
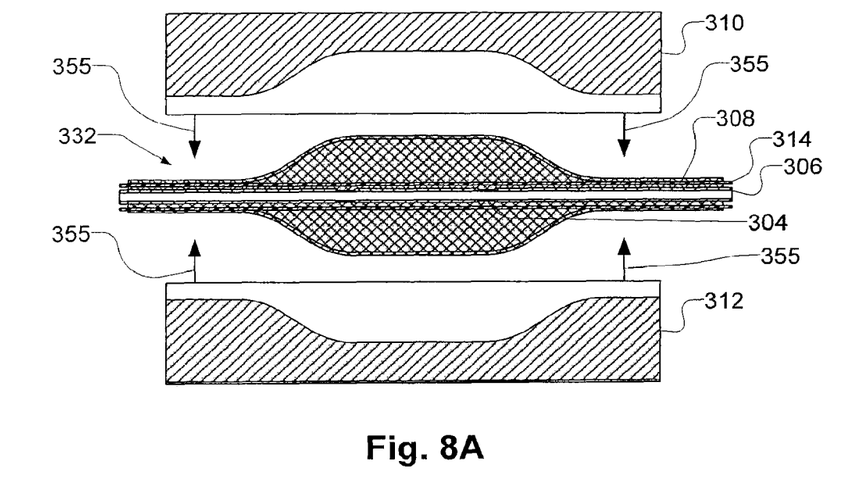
FIGS. 8A-8C illustrate steps in the manufacture of a composite balloon according to the embodiment of FIG. 7.
Figure 8B:
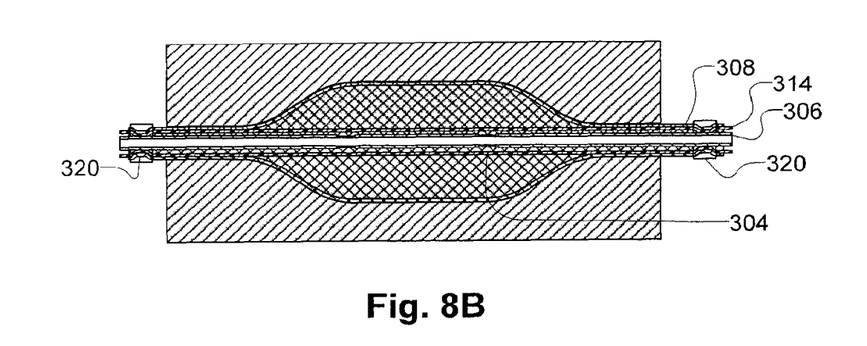
Figure 8C:
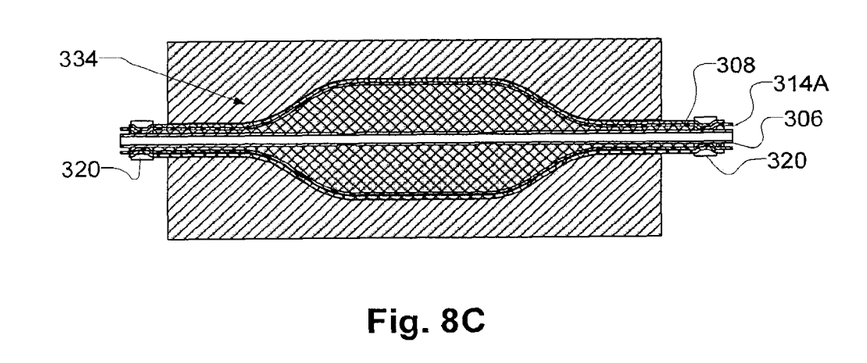

FIG. 6C is a flow diagram of a method for making a reinforced medical balloon using a liner balloon as a form. In step S210, the liner balloon 220 (FIG. 5C) is fabricated and in step S215, a braiding device is used to braid over the liner balloon 220 (FIG. 5C). In step S235, a cylindrical mandrel may be inserted in the liner to help seal and fill the balloon and the subassembly inserted in a mold. In step S240, in this embodiment, the liner is inflated with a pressurized fluid and the subassembly is heated until the braid is melted into the liner balloon, which thereby forms a matrix that seals the braided structure. The matrix is then cooled in step S245 to form an integral structure.

In the foregoing embodiments, the method steps were deliberately varied to illustrate that there are multiple ways to form the balloon with an integrated fiber braid reinforcement. For example in the methods of FIGS. 6A and 6B, a curable coating is placed on a preform while in FIG. 6C, a liner of thermoplastic is partially melted and cooled to form the balloon. It will be recognized that the various methods and features can be altered and varied to form balloons and that no particular method is required to realized the benefits of the reinforcement structure described in the instant application. For example, the fibers that are braided may be coated, or the preform impregnated with finely divided thermoplastic or adhesive with the liner balloon being of a high melting temperature than the molding temperature. Then in the method of FIG. 6C, the coating or impregnated material would then adhere the braid to the liner to form the balloon during thermal molding.

An alternative method of making a balloon without employing a mold is to braid over a liner balloon using yarns that contain resin that flows at a lower temperature than the base material of the yarns of the base balloon. For example high melting-temperature yarns may be coated with low melting-temperature thermoplastic. After braiding over the base balloon with the two-part yarns, the braid and base balloon may be heated to a temperature that causes the low melting-temperature resin to flow sealing any openings between the yarns. The base balloon material and thickness may be chosen such that it may either be removed or left in place depending on the properties of the material of the base balloon.

FIG. 7 and FIGS. 8A, 8B, and 8C illustrate the manufacture of a composite balloon according to an embodiment. A mandrel 302 with openings 304 is inserted in a tube 314 of Polyethylene Terephthalate (PET), Nylon, or other suitable material, that will be molded to form a balloon liner. The mandrel 302 and tube 314 are inserted in a braided preform 308 and the substructure 332 then placed in a mold 310, 312, here illustrated as a two part mold. See FIG. 8A. Clamps 320 are placed over the ends of the mandrel 306 to seal the tube 314 and preform 308 against the mandrel 306. The mold is then assembled (as indicated by broken lines 322 or arrows 355) and compressed over the preform 308 (See FIG. 8B) and heated while air or other fluid is injected in the mandrel 302 at an end opening 306. As a result the tube 314 balloon is softened and expands under pressure. See FIG. 8C. After the tube 314, now a balloon 314A, has formed a composite balloon 314, the mold is cooled and the composite balloon 314 is removed.

Figure 9A:
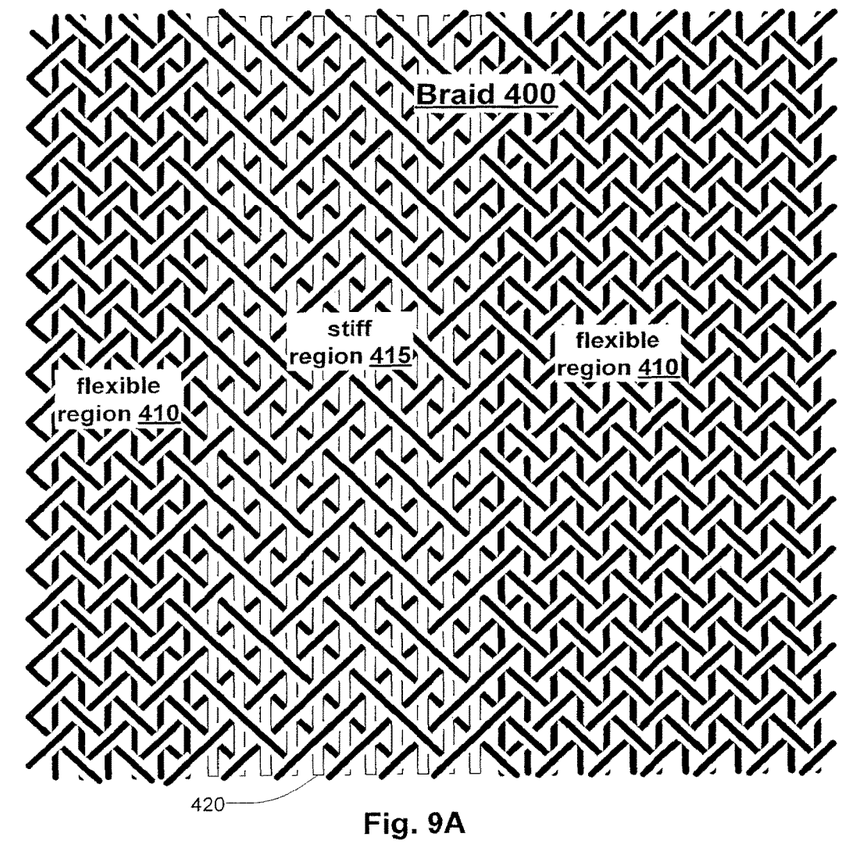
FIGS. 9A-9C illustrate a braiding pattern and yarn set that provides relatively stiff and relatively pliable portions.
Figure 9B:
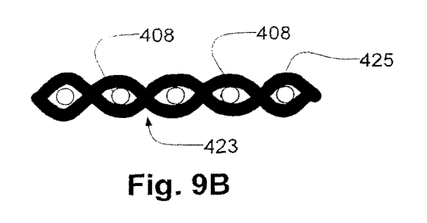
Figure 9C:
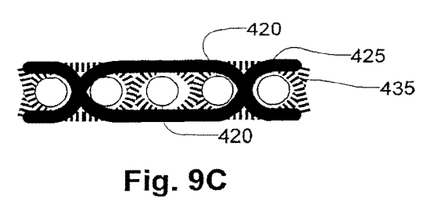

FIGS. 9A-9C illustrate a braiding pattern and yarn set that provides relatively stiff and relatively pliable portions. The present embodiment is similar to that of FIGS. 4A-4C except that the 0° yarns 420 are larger in cross-section than the other yarns within the stiff regions 415. In the flexible regions 410 the yarns may be identical. The 0° yarns 420 in the present embodiment have the effect of separating the tension portions 420 further apart than the embodiment of FIGS. 4A-4C thereby creating even greater stiffness.

In FIG. 9B, the relatively flexible diamond pattern is shown in a figurative cross-section with the 0° yarns 408, shown in section. Again, the seams, such as indicated at 423, where yarns 425 cross, are longitudinally arranged because yarns 425 alternate at every crossing. In FIG. 9C, where yarns 425 do not alternate at every crossing, a less flexible structure is formed with crossing yarns 420 forming tension elements as described above with reference to FIG. 4C. Again, preferably, the braid pattern is such that stiff segments are offset and staggered in a direction perpendicular to the longitudinal direction to provide a cooperative continuous extension of the stiffness between stiff segments. Such a staggered arrangement is illustrated in FIG. 9C by observing the positions of the alternation points of other crossing yarns 435, which do not coincide in the lateral direction.

Note that another embodiment of a braid may that employs a biaxial braid structure may be created, which uses the same principle. In such an embodiment, no 0° yarns exist in the flexible regions 410 but 0° elements—not necessarily yarns—serve to separate the biaxial layers of biaxial yarns in stiff regions. In such an embodiment, the elements 420 could be, for example, PET or Nylon filaments. In this case, the 0° elements may be of another material that helps to provide the resistance to compression along with the material that forms the matrix.

Figure 10:
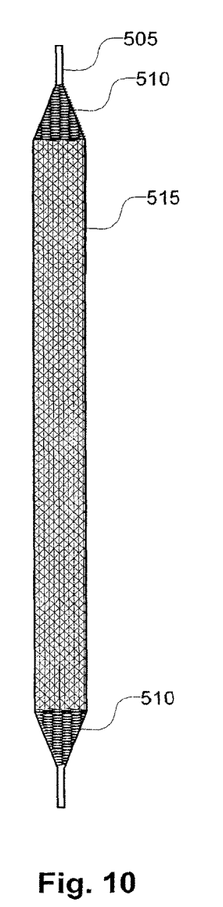
FIG. 10 illustrates a balloon embodiment in which reinforcement portions are added in stages and sections.

FIG. 10 illustrates a balloon embodiment in which reinforcement portions are added in stages and sections. Instead of braiding over a form to create a three-dimensional preform, the braiding structures described herein may be braided as a cylindrical tube 515. The tube 515 may be slid over a balloon 505 and bonded or molded to it. In that case, the end portions may be formed by teasing the braid, folding it over (lapping it), cutting notches in it, or simply terminating it before completely covering the ends. In addition, braid may be formed over the ends as indicated at 510. For example, the tube 515 may be teased and the fibers laid over the end (which is conical in the example) and a helical wind may be wrapped over the conical ends. See U.S. Pat. No. 6,746,425 for Medical Balloon; hereby incorporated by reference as if fully set forth herein; which describes a structure and method for wrapping a balloon with a helical wind. For example, the method which may involve the use of adhesive according to an embodiment in the reference, may be followed after the tube braid 515 is laid over a liner balloon and inflated to form the desired shape.

In variation on the embodiment of FIG. 10, 0° yarns may be extended beyond the end of the tube where the conical end portion is reached. These free longitudinal fibers may be adhesively bonded in place as described in U.S. Pat. No. 6,746,425 and a helical wind added over the top in the manner described in this patent. The free ends of the 0° yarns may be obtained by the braiding device or by cutting the or unraveling. Alternatively, the diagonal yarns may be included in the longitudinal reinforcements over the conical portions.

Figure 11:
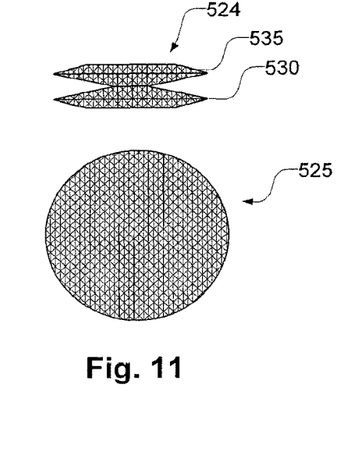
FIG. 11 illustrates a reinforced balloon having a non-cylindrical shape.

FIG. 11 illustrates a reinforced balloon having a non-cylindrical shape. FIG. 11 is included to illustrate that the inventive reinforcement structures are not limited to cylindrical balloons. For example, a balloon 524 that collapses using accordion folds 530 and 535 and inflates to an expanded shape such as a cylinder may be formed.

Figure 12:
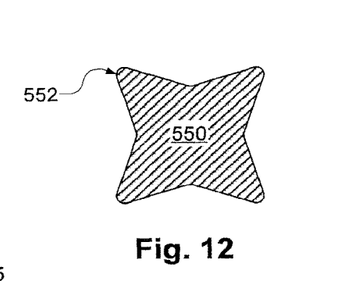
FIG. 12 illustrates a cylindrical form with a non-circular cross-section.
Figure 13:
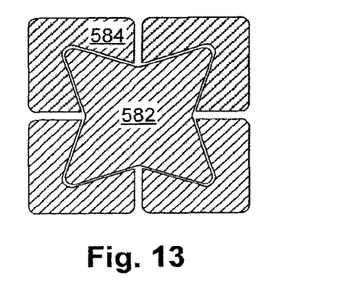
FIG. 13 illustrates a molding apparatus for forming reinforcement structures or combinations of balloons and reinforcement structures.

FIG. 12 shows a cylindrical form 550 with a non-circular cross-section. It may be beneficial to braid over such a non-cylindrical form, in some cases, to further promote folding, depending on the compatibility with yarn angles and other considerations. By braiding over such a form, the lengths of yarns are biased to favor the folded configuration, which is a property that is in addition to the variegated stiff and flexible regions property discussed above. The cylinder 550 (note that technically, non-circular column shapes are still called "cylinders") may have a helical wind to it if the fold lines are not longitudinal. In some cases, it may be beneficial to use a stiffer braid throughout the entire braided structure (for example as described with reference to FIGS. 4A-4C and FIGS. 9A-9C), which would result in shorter tension members 284 and 420 adjacent the sharp bends 552 (typ.) than in the layer remote from it. Thus, such a structure would retain a bias toward its folded configuration as if the braid were "molded" or annealed to be in its most relaxed state when folded. FIG. 13 illustrates a molding apparatus for forming reinforcement structures or combinations of balloons and reinforcement structures. The mold includes a central portion 582 and a wing portions 584. Using such a structure, a balloon can have a folded shape bias molded into the matrix as well as the properties of additional flexibility in the folded portions, and/or folded bias, in the composite substructure (e.g., the braid).

Figure 14:
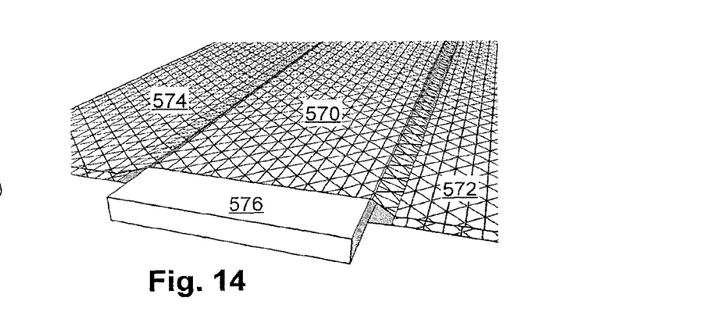
FIG. 14 illustrates another braiding pattern and structure that provides relatively stiff and relatively pliable portions.

FIG. 14 illustrates another braiding pattern and structure that provides relatively stiff and relatively pliable portions. Here, a stiff region 570 has a spacer 576 over which the braid is woven. The spacer 576 may be held as a 0° yarn and braiding may be performed around it. The layers of the flexible regions 572 are adjacent to allow them to be more flexible. The separated layers of the stiff region 570 contribute stiffness in a manner similar to that described with reference to FIGS. 4B-4C and FIGS. 9B-9C. That is the upper layer and lower layers act as tension elements over an incompressible core in the form of the spacer 576. Note that the layers in the flexible regions 574 may be woven into a single fabric using three-dimensional braiding equipment. See for example, three dimensional braiding as described in U.S. Pat. Nos. 5,357,839; 5,772,848; and 6,090,137, hereby incorporated by reference as if fully set forth herein.

Figure 15:
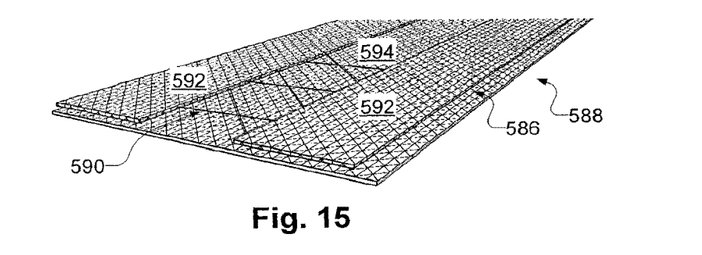
FIG. 15 illustrates yet another braiding pattern that provides relatively stiff and relatively pliable portions.

FIG. 15 illustrates yet another braiding pattern that provides relatively stiff and relatively pliable portions. The stiff portions 592 are formed by overbraiding (braiding on top of a braid to form an additional layer) with an overbraided layer 586 in only the regions 592 that are to be stiffened. This may be done using less expensive two-dimensional braiding equipment. The braid pattern may include yarns 590 that connect the overbraided layers 586. The thin region is defined mostly by the lower layer 588. In another embodiment, a spacer such as 576 in FIG. 14 is included between the layers in the stiff regions. Note in this embodiment, a spacer may be included by an intermediate lamination or coating step in which the spacer is placed on a balloon rather than being positioned and included as part of a braid preform.

In a preferred embodiment, the stiff portions 592 can be made of a radio-opaque material to enhance visualization of the balloon in situ. Alternatively, the stiff portions 592 can have a radio-opaque material integrated into them or coated on them to make them radio-opaque. This may allow the use of radio-opaque materials which might be too inflexible or otherwise difficult to integrate in a medical balloon.

In any of the embodiments described herein, the balloon may be coated or impregnated with a radio-opaque material or have the radio-opaque material otherwise integrated into them, such as by the braiding process as discussed in the instant specification. Such radio-opaque materials can be restricted the relatively flat (non-folding) portions of the balloon wall which may permit the use of materials that cannot tolerate as high a degree of strain if used in portions that are folded tightly.

Examples of materials that may be used for the matrix and or liner of the above embodiments include polycaprolactam, polyesters, polyethers, polyamides, polyurethanes, polyimides, ABS copolymers, polyester/polyether block copolymers, ionomer resins, liquid crystal polymers, and rigid rod polymers.

Applications of the medical balloon embodiments include vascular dilatation, stent delivery, drug delivery, delivery and operation of sensors and surgical devices such as blades, and the like. Exemplary design parameters of balloons within the scope of the invention include balloons with burst pressures of 100 psi or more.

Note that although many of the examples discussed and illustrated above were based on triaxial braid structures, biaxial the benefits of the inventive embodiments may be applied to other braid patterns. Such patterns include multilayer and so-called thick braids or three-dimensional braids.

Also note that there are types of braiding technology that allow a high degree of flexibility and control for forming braids. Suitable technology and techniques as may be combined with the teachings of this disclosure may be found in: U.S. Pat. Nos. 5,085,252; 5,465,760; 6,129,122; 6,315,007; and 6,439,096, which are hereby incorporated by reference as if fully set forth herein.

Also note that although the embodiments are described in terms of braids as a base technology, it possible to achieve the same benefits using a weaving or combination weaving and braiding technology. In such cases the stiffening properties may be derive from warp and/or weft yarns in a fabric weave. Moreover, current technologies for knitting, weaving, and braiding have blurred the boundaries of these categories so the terms should not be taken as limiting.

In the instant disclosure, the words "yarn" and "fiber" are used interchangeably. The term "yarn" is commonly used in the field of braiding. The term is not intended to limit the material, composition, or structure of the fiber material that is used in any of the above-described embodiments. In addition, the structures disclosed may be created in various ways including mechanisms that do not include braiding. Thus, even where the term "yarn" is used and/or where braiding is described as a preferred means of forming a structure, the uses are not necessarily intended to limit the structures described to ones formed by braiding.

A variety of materials can be used for the fibers/yarns. Examples include, but are not limited to, high strength inelastic fibers such as Kevlar, Vectran, Spectra, Dacron, Dyneema, Teflon (PBT), Zylon (PBO), Polyimide (PIM), ultra high molecular weight polyethylene, and the like. In addition, fibers/yarns may have non-circular cross-sections. For example, flat fibers/yarns may provide superior amenability to folding.

In any of the above embodiments, the balloon or the braid pre-form can be coated with suitable materials (paint) to render the resulting medical balloon radio-opaque. Suitable coatings are known, for example, as discussed in U.S. Pat. No. 6,599,448, hereby incorporated by reference as if fully set forth herein. In addition, some or all of the yarns or fibers employed may be radio-opaque to enhance the radio-opacity of the resulting balloon. This can be performed, for example, by applying a coating to the balloon, or fibers using vapor deposition or electro-energy deposition, for example, a metal coating such as tantalum or other materials such as barium sulfate. Also, a metallic layer can be used in treatment such as to provide a means for creating an electric field inside the body for sterilizing a site. Examples of such applications and biocides are described in U.S. Pat. No. 6,258,249 (Charles Lee Simpson for "Sterilization of surgical sites") which is incorporated by reference as fully set forth herein.

Figure 16:
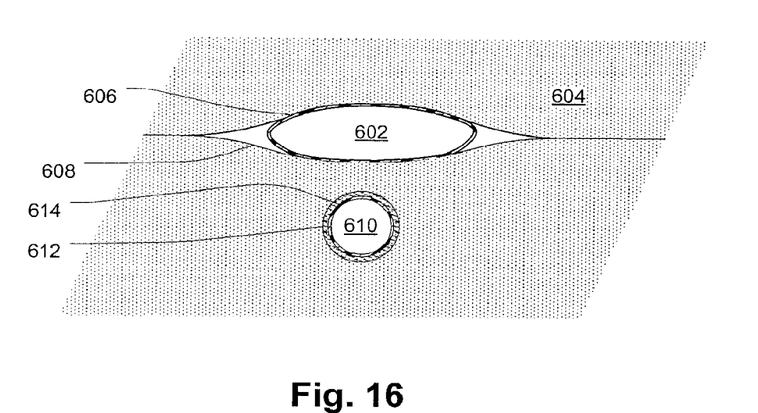
FIG. 16 illustrates two alternative types of balloons inserted in an opening of a host.

Referring now to FIG. 16, a medical balloon 601 may be of any suitable structure including monolithic polymer, composite with fibers, including braided fibers, laminates, or any other suitable structure. The medical balloon 601 has conductive surfaces (not shown in this view) on its external surfaces to allow the generation of an electric field for performing the biocidal function described in U.S. Pat. No. 6,258,249 incorporated by reference above. In the example shown, the balloon 601 is inserted between two surfaces 606 and 608 of a body cavity, a surgical or traumatic wound in a host 604. The balloon 601 may be coated with a biocide as described in U.S. Pat. No. 6,258,249 and the conductive surfaces connected to a source of voltage (alternating or direct) to destroy biofilm or other susceptible infectious material. The balloon 601 may be inserted and moved around, with an internal pressure that allows the balloon 6021 to conform to the surfaces 606 and 608. A cylindrical balloon 614 may be inserted in a lumen structure 616 of the host 604 to perform the same function. For example, the lumen could be a blood vessel, a urethra, a duct, or any other cylindrical cavity or conduit. The internal space 602, 610 of either balloon 601, 614 can be filled with any suitable material such as, for example, saline.

Figure 17A:
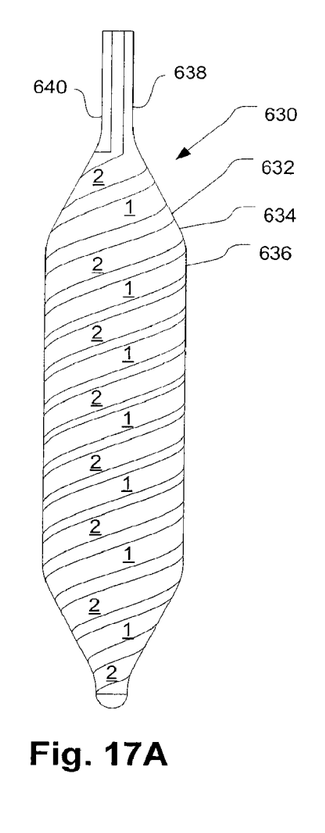
FIGS. 17A and 17B illustrate embodiments of a medical balloon embodiments with conducting surfaces for use in biocidal procedures or other procedures where balloons having conductors are used.
Figure 17B:
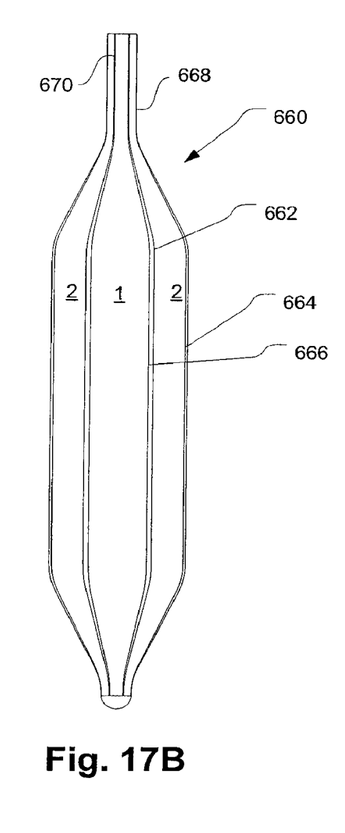
Figure 18:
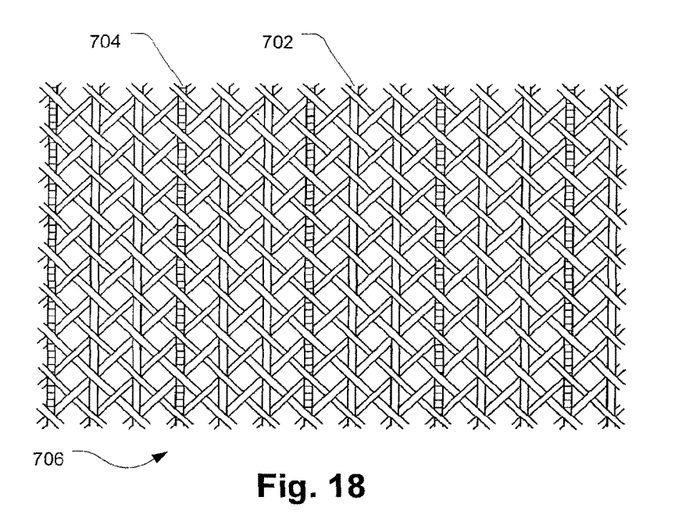
FIG. 18 illustrates a fabric with conductive yarns.
Figure 19:
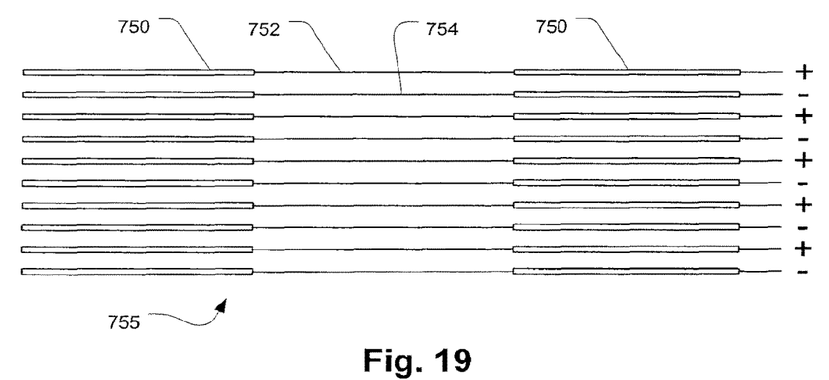
FIG. 19 illustrates partly insulated conductive yarns for use with embodiments of the invention.
Figure 20:
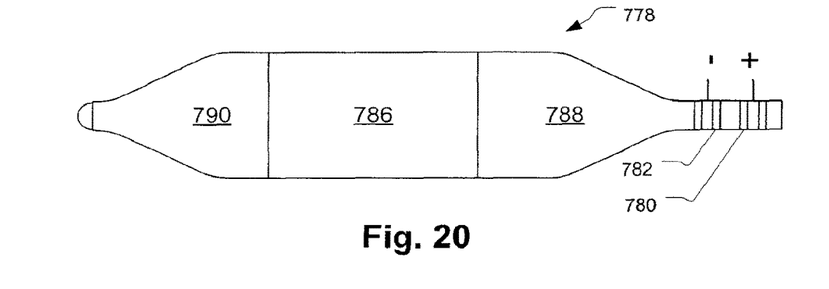
FIG. 20 illustrates a balloon with partly insulated conductive yarns.

Further details of the balloons of FIG. 16 are shown in FIGS. 17A, 17B, as well as FIGS. 18 through 20, according to various alternative embodiments. Referring now to FIGS. 17A and 17B, the surface of balloons 630 and 660 are striped with first and second conductive strips 634 and 636 for balloon 630 and 664 and 666 for balloon 660. The strips are labeled 1 and 2 to indicate which of two poles of a voltage source (not shown) they are connected to. The strips 634 and 638 or 664 and 666 can be painted, sputtered, laminated, or otherwise deposited on the balloon in any suitable manner.

In an alternative embodiment, the strips 634 and 638 or 664 and 666 may be realized by employing conductive yarns in a braid pattern whose surface is exposed on the balloon 630, 660. The surface may be exposed by creating a braided preform in which parallel sets of conductive yarns are used. Then a base balloon with an adhesive, for example, a thermally activated adhesive or thermopolymer layer, may be inflated within the pre-form. The adhesive may not be required depending on the requirements of the application, but the result is preferably one in which the conductive yarns are exposed on the surface of the balloon to create the patterns shown in FIGS. 17A and 17B. The conductive surfaces of the balloon 630 and 660 may be carried to terminals 638, 640 or 668, 670, respectively, for connection to the voltage source.

FIG. 18 shows an example of parallel conductive yarns, in this case, the longitudinal yarns 704 are held in position and maintained parallel by the triaxial braiding pattern of the fabric 706. The conductive yarns 704 may be interspersed with non-conductive yarns. In alternative embodiments, some or all of the diagonal yarns 703 may be made conductive. The polarity may alternate as every N yarns in any desired manner to achieve a desired spacing of the oppositely polarized yarns. Note that the conductive yarns may be of metal, carbon-impregnated fiber, carbon composite, or any suitable material. Note also that a braid is not required to employ conductive fibers in this manner. For example yarns can be laid into a mold and a balloon molded into it as described in U.S. Pat. No. 6,746,425, hereby incorporated by reference as if fully set forth herein. Any adhesive or matrix remaining on the surface can be polished off to expose the conductive yarns.

Referring to FIGS. 19 and 20, the conductive yarns can be provided with insulation in parts to provide that the conductors are exposed only at desired locations on a balloon. For example, conductors 752 and 754 (which indicate sets of alternating polarity), in the array 706, depicted in FIG. 19, are exposed only in a region 756 (or 786 in the FIG. 19 embodiment). A region 757 exposes the conductors 752 and 754 at a terminal region 757 for connection to a source. The conductors 752 of one polarity may be exposed by lack of insulation in a different axial position than the conductors 754 of the other polarity to facilitate connection to voltage sources as illustrated in FIG. 20. Here, region 782 is a region in which the yarns of one polarity are exposed and the yarns of the other polarity are insulated. Region 780 is a region in which the yarns of the other polarity are exposed and the yarns of the one polarity are insulated. In this way conductive take-offs 781 and 783, can be soldered or otherwise electrically connected to the conductive yarns without causing shorting.

While the present invention has been disclosed with reference to certain preferred embodiments, numerous modifications, alterations, and changes to the described embodiments are possible without departing from the sphere and scope of the present invention, which is described, by way of example, in the appended numbered paragraphs below. Accordingly, it is intended that the present invention not be limited to the described embodiments, but that it have the full scope defined by the language of at least the following claims and equivalents thereof.

The invention claimed is:

1. A foldable composite balloon, comprising:
   a body with a polymer matrix and a plurality of filaments attached thereto;
   the body having first and second portions and a folding line lying within the second portions;
   the plurality of filaments being configured to promote folding along the folding line either by being configured to:
   cause the body to be stiffer in the first portions, at least in a direction perpendicular to the folding line, than in the second portions; or
   generate a mechanical bias that favors folding along the folding line rather than the first portion, the bias resulting from tension in the plurality of filaments from the body being formed over a form with edges thereon.

2. A balloon as in claim 1, wherein the plurality of filaments is configured to cause the body to be stiffer in the first portions, at least in a direction perpendicular to the folding lines, than the second portions.

3. A balloon as in claim 1, wherein the plurality of filaments includes a braid.

4. A balloon as in claim 1, wherein the plurality of filaments has first and second filaments and compression elements, the first portions being stiffer, at least in a direction perpendicular to the folding lines, at least in part as a result of the first and second filaments of the first portions being arranged with the compression elements between them, thereby defining opposing tension elements separated by the compression elements.

5. A balloon as in claim 4, wherein the first and second filaments define a braid.

6. A balloon as in claim 4, wherein the plurality of filaments includes a braid with layers, the braid having more layers in the first portions than in the second portions such that the first portions are stiffer than the second portions.

7. A balloon as in claim 1, wherein the body has a longitudinal axis and the folding lines are parallel to the longitudinal axis.

8. A balloon as in claim 1, wherein the body has a longitudinal axis and the folding lines wind helically around a longitudinal axis.

9. A balloon as in claim 1, wherein the plurality of filaments includes one of a triaxial and biaxial braid.

* * * * *